United States Patent [19]

Chekroun et al.

[11] Patent Number: 4,487,931
[45] Date of Patent: Dec. 11, 1984

[54] PROCESS FOR THE PREPARATION OF 2-(THIEN-2-YL)- AND 2-(THIEN-3-YL)-ETHYLAMINE DERIVATIVES

[75] Inventors: Isaac Chekroun, Toulouse; Alain Heymès, Sisteron, both of France

[73] Assignee: Sanofi, Toulouse, France

[21] Appl. No.: 393,384

[22] Filed: Jun. 29, 1982

[30] Foreign Application Priority Data

Jun. 30, 1981 [FR] France .................. 81 13063

[51] Int. Cl.³ .................. C07D 409/12; C07D 333/20
[52] U.S. Cl. .................. 546/280; 549/59; 549/60; 549/61; 549/68; 549/71
[58] Field of Search .................. 546/280; 549/59, 60, 549/61, 68, 71

[56] References Cited

U.S. PATENT DOCUMENTS 4,127,580 11/1978 Braye .................. 546/114

OTHER PUBLICATIONS

Burger, Medicinal Chemistry, Second Edition, pp. 78–79, Interscience Publishers, RS 403 B–8, C.7, (1960).

*Primary Examiner*—Alan L. Rotman
*Attorney, Agent, or Firm*—Weiser & Stapler

[57] ABSTRACT

The present invention provides a multistep process for the preparation of 2-(thien-2-yl)- and 2-(thien-3-yl)-ethylamine intermediates of the general formula:-

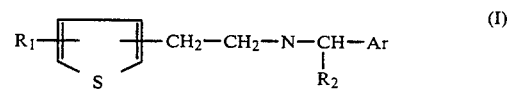

(I)

in which $R_1$, in the 2-, 3-, 4- or 5-position, is a hydrogen or halogen atom, a nitro, amino, cyano or carboxyl group, a linear or branched alkyl or alkoxy radical or a heterocyclic or non-heterocyclic aromatic radical, which is optionally mono- or polysubstituted, $R_2$ is a hydrogen atom, a linear or branched alkyl radical or a heterocyclic or non-heterocyclic aromatic radical, which is optionally mono- or polysubstituted, and Ar is a heterocyclic or non-heterocyclic aromatic radical, which is optionally mono- or polysubstituted, when the aminoethyl radical is in the two position and the radical $R_1$ is in the 4- or 5-position, the above intermediates can be converted into 4,5,6,7-tetrahydrothieno[3,2-c]pyridine derivatives according to a procedure set forth in U.S. Pat. No. 4,127,580. When the aminoethyl radical is in the 3-position and the radical $R_1$ is in the 4- or 5-position, the above intermediates can be converted into 4,5,6,7-tetrahydrothieno[2,3-c]pyridine derivatives according to a procedure set forth in U.S. Pat. No. 4,127,580. Both sets of tetrahydrothieno pyridine final products possess anti-inflammatory, vasodilator and blood platelet aggregation inhibition activity.

10 Claims, No Drawings

PROCESS FOR THE PREPARATION OF 2-(THIEN-2-YL)- AND 2-(THIEN-3-YL)-ETHYLAMINE DERIVATIVES

The present invention is concerned with a new process for the preparation of thienylamines.

The thienylamines with which the present invention is concerned are compounds of the general formula:

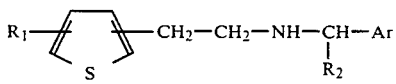
(I)

in which $R_1$, in the 2-, 3-, 4- or 5-position, is a hydrogen atom, a linear or branched alkyl radical or a heterocyclic or non-heterocyclic aromatic radical, such as a thienyl, furfuryl, pyridyl, phenyl or naphthyl radical, optionally mono- or polysubstituted by substituents such as alkyl, phenyl, halogen, nitro, cyano, amino, carboxy or alkoxy groups or the like, or $R_1$ is an alkoxy radical, a halogen atom or a nitro, carboxyl, cyano or amino radical or the like; the aminoethyl chain is in the 2- or 3-position of the thiophene nucleus; $R_2$ is a hydrogen atom, a linear or branched alkyl radical or a heterocyclic or non-heterocyclic aromatic radical, such as a thienyl, furyl, pyridyl, phenyl or naphthyl radical, optionally mono- or polysubstituted by substituents such as alkyl, phenyl, halogen, nitro, cyano, amino, carboxyl or alkoxy groups or the like; and Ar is an aromatic radical such as described above.

A certain number of derivatives corresponding to general formula (I) are known and used as intermediates in the preparation of compounds employed both in the chemical industry and in the pharmaceutical industry.

Thus, by way of example, amongst the derivatives obtained in accordance with the new process, there may be mentioned those which can lead, by known means, on the one hand (when the aminoethyl chain is in the 2-position and the radical $R_1$ is in the 4- or 5-position) to 4,5,6,7-tetrahydrothieno[3,2-c]pyridine derivatives and, on the other hand (when the aminoethyl chain is in the 3-position and the radical $R_1$ is in the 4- or 5- position) to 4,5,6,7-tetrahydrothieno[2,3-c]pyridine derivatives; in both cases, these derivatives have formed the subject of several of our earlier French Patents, namely, Nos. 73/03,503, 75/03,968, 75/20 241, 75/23,786, 75/24,486, 76/00,003 and 77/21,517, for their therapeutic use and/or processes for the preparation thereof.

The present invention provides a process, which is simple and inexpensive compared with the prior art, for the preparation of compounds of the general formula (I).

According to the process of the present invention, in order to prepare the derivatives of general formula (I):

(a) a derivative of the general formula:

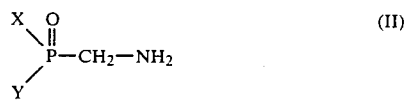
(II)

in which X and Y, which can be the same or different, are alkyl, aryl, alkoxy, aryloxy, dialkylamino or diarylamino radicals so that the organophosphorus compound of general formula (II) can be, fo example, a phosphonate, a phosphinate, a phosphine oxide or a phosphonamide, is condensed with a carbonyl compound of the general formula:

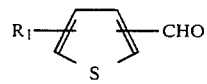
(III)

in which $R_1$ is as defined in general formula (I), to give a compound of the general formula:

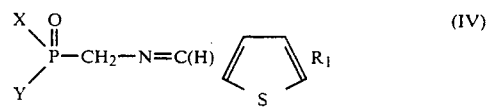
(IV)

in which $R_1$, X and Y have the same meanings as above;

(b) the compound of general formula (V) is treated with a base of the general formula $B^{\ominus}M^{\oplus}$ to give a carbanion of the general formula:

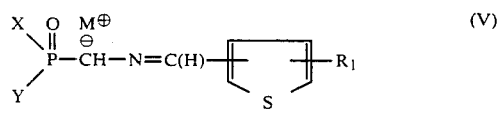
(V)

in which X, Y and $R_1$ have the same meanings as above;

(c) the carbanion of general formula (V) is converted by the action of heat into a derivative of the general formula:

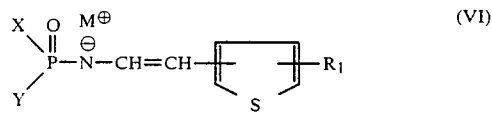
(VI)

in which X, Y and $R_1$ have the same meanings as above, which, after taking-up in water, gives a compound of the general formula:

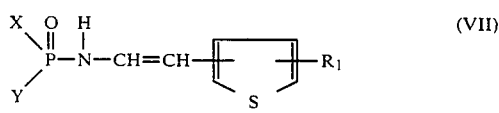
(VII)

in which X, Y and $R_1$ have the same meanings as above, this reaction generally being carried out at a temperature of from $-78°$ C. to $+150°$ C., which is chosen, more specifically, as a function of the base $B^{\ominus}M^{\oplus}$, to be on the whole at the top of the range, particularly when carrying out stage c;

(d) the compound of general formula (VII) is reacted successively with a base of the general formula $B'^{\ominus}M'^{\oplus}$ and then with a carbonyl compound of the general formula:

(VIII)

in which Ar and $R_2$ are as defined in general formula (I), to give a compound of the general formula:

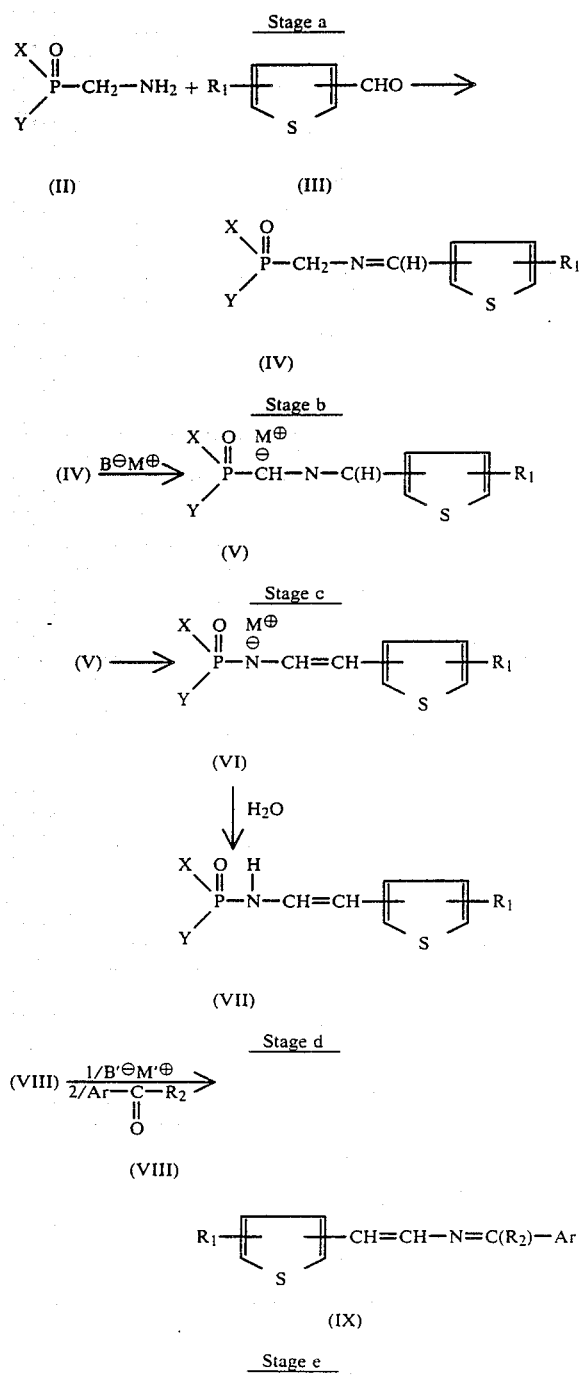

in which $R_1$, $R_2$ and Ar have the same meanings as above; and (e) the derivative of general formula (IX) is finally converted into a compound of general formula (I) as defined above by reaction with a reducing agent, such as, in particular, an alkali metal borohydride.

The process according to the present invention can be illustrated by the following reaction scheme:

The process can advantageously be carried out as follows:

(a) The organophosphorus compounds of general formula (II), which are readily obtainable by well-known processes of preparation, for example, the one described by I. C. Popoff et al. (J. Org. Chem., 28, 2898/1963), can be reacted with the carbonyl derivatives (III) in the absence of a solvent and of a catalyst, the water formed during the reaction being removed at the end of the operation by appropriate means. The condensation can advantageously be carried out in a solvent, such as an aromatic hydrocarbon, for example toluene, or an alcohol, for example ethanol, by means of which it is possible to remove the water by azeotropic distillation. It can also be advantageous (from the point of view of the speed) to carry out the condensation in the presence of catalytic amounts of a mineral or organic acid, for example p-toluenesulphonic acid. The temperature at which this conversion is carried out can vary but, generally, is from 20° to 120° C.

(b), (c) The base $B^-M^+$ used in this stage can be an alkali metal hydride, especially sodium, lithium or potassium hydride, an alkali metal amide or alkylamide, especially an alkali metal dialkylamide, such as lithium diisopropylamide, or an organo metallic ccompound, especially an organolithium, such as n-butyllithium, or an organosodium or organomagnesium. It is also possible to use alkali metal or alkaline earth metal alcoholates, such as sodium, lithium, potassium or magnesium methylate, potassium tert.-butylate or sodium tert.-amulate. It is also possible to use alkali metal or alkaline earth metal hydroxides, such as sodium, lithium, potassium or magnesium hydroxide.

In general, one stoichiometric equivalent of the base $B^{\ominus}M^{\oplus}$, or even a slight excess, for example an excess of 10%, relative to equivalence, is used. However, it is also possible to use amounts of base which are lower or even substantially lower than stoichiometric equivalence.

It should be emphasized that, according to a variant of the present invention, when one stoichiometric equivalent of the base $B^{\ominus}M^{\oplus}$ is used, it can be advantageous to avoid the isolation of the derivative (VII) and to react (VI) directly with the carbonyl compound VIII), thus also avoiding the use of the base $B'^{\ominus}M'^{\oplus}$.

The reaction is generally carried out at a temperature of from −78° C. to +150° C., the temperature being chosen, more specifically, as a function of the base $B^{\ominus}M^{\oplus}$ to be on the whole at the top of the range, especially when carrying out stage (c).

The preferred solvents are linear or cyclic ethers, such as tetrahydrofuran, hydrocarbons, in particular aromatics, such as benzene, toluene and xylenes, alcohols, amides, in particular dimethylformamide, and sulphoxides, in particular dimethyl sulphoxide. It can also be advantageous, especially if metal hydroxides are used, to carry out the reaction in a two-phase system (water+a solvent, such as a halogen-containing solvent, for example methylene chloride, or an aromatic hydrocarbon, such as benzene, toluene or xylenes) in the presence of a phase-transfer catalyst, especially a quaternary ammonium salt, such as tetra-n-butylammonium iodide, or a phosphonium salt. The usual methods can be used to isolate the compound (VII).

(d) The base B'⊖M'⊕ used in the first part of this third stage can be chosen from amongst those listed under (b) above. In general, it is used in stoichiometric equivalence but can be in slight excess, for example in an excess of 5 to 10%, relative to this equivalence.

The reaction is generally carried out at a temperature of from −20° C. to +100° C., the bottom of the range being preferred. The solvents used are those described in stage (b) above.

In the second part of this stage, the carbonyl compound of general formula (VIII) is reacted with the reaction mixture such as defined above at a temperature which is generally similar to that of the first part.

(e) The reduction of the derivative of general formula (IX) is advantageously carried out with a mixed alkali metal hydride, especially a borohydride, for example sodium or potassium borohydride. The reduction is carried out in an inert solvent, such as an ether, for example tetrahydrofuran or dioxan, or in an alcohol, for example, methanol or ethanol.

In certain cases, and especially where R₂ is not a hydrogen atom, it can be advantageous to add one molar equivalent, relative to the borohydride used, of an organic acid, for example, acetic acid or trifluoroacetic acid, to the reaction medium.

It is also possible to carry out this reduction by means of catalytic hydrogenation in a homogeneous or heterogeneous phase under conditions which are generally well known.

The compounds of general formula (I) thus obtained can then be isolated and purified in accordance with the usual methods. To carry out these operations, it can be advantageous to convert the free bases of general formula (I) into their salts, for example their acid-addition salts, by reaction with mineral or organic acids. The compounds of general formula (I) can be freed from the salts by known methods.

The present invention also includes the intermediates obtained at the various stages of the synthesis: compounds of the general formula:

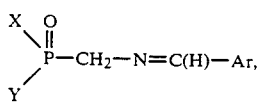           (IV)

compounds of the general formula:

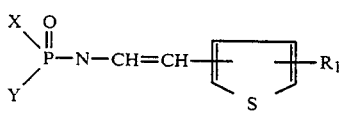           (VII)

compounds of the general formula:

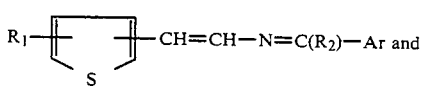   and     (IX)

compounds of the general formula:

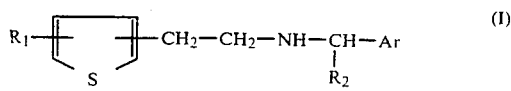           (I)

The following Examples are given for the purpose of illustrating the present invention:

EXAMPLE 1

Preparation of N-(o-chlorobenzyl)-2-(thien-2-yl)-ethylamine hydrochloride

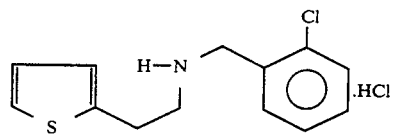

Stage a

Diethyl N-thien-2-ylidene-aminomethylphosphonate

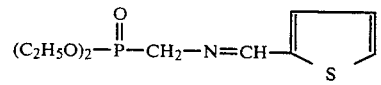

A solution of 16.7 g. (0.1 mol) diethyl aminomethylphosphonate in 200 ml. absolute ethanol is treated with 11.2 g. (0.1 mol) thien-2-aldehyde and the mixture is heated under reflux and then evaporated to give 26 g. diethyl N-(thien-2-ylidene)-aminomethylphosphonate (yield: about 100%) in the form of a yellow oil giving a single spot in TLC (silica plate; eluent: ethyl acetate).

IR film
C═N 1640 cm⁻¹
P═O 1260 cm⁻¹
P—O—C 1060–1080 cm⁻¹
NMR (CDCl₃) δ/TMS
1.35 ppm (t, 6H)
3.9 to 4.45 ppm (m, 6H)
7 to 7.8 ppm (m, 3H)
8.5 ppm (d, 1H)

Stages b, c and d 1-(o-Chlorophenyl)-4-(thien-2-yl)-2-azabuta-1,3-diene

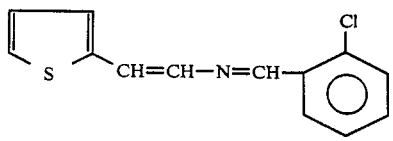

A solution of 27.9 g. (0.1 mol) diethyl N-(thien-2-ylidene)-aminomethylphosphonate in 40 ml. of tetrahydrofuran is added dropwise to a suspension of 11.2 g. (0.1 mol) potassium tert.-butylate in 160 ml. of tetrahydrofuran. During the addition, the temperature rises from 20° to 35° C. When the addition has ended, the reaction mixture is heated at 40° to 45° C. for 30 minutes and a solution of 14.05 g. (0.1 mol) o-chlorobenzaldehyde in 10 ml. tetrahydrofuran is then added dropwise. The reaction is left to continue for one hour and the tetrahydrofuran is then evaporated off. The residue is taken up in diethyl ether and water and the aqueous phase is re-extracted with diethyl ether. The combined ether phases are washed with water, dried over anhydrous sodium sulphate and evaporated to give 17.8 g. (yield: 72%) of 1-(o-chlorophenyl)-4-(thien-2-yl)-2-azabuta-1,3-diene in the form of an orange oil, which is used as such in the following stage.

IR (film):
C=N 1640 cm$^{-1}$
NMR (CDCl$_3$) CH=N
8.6 ppm (s, 1H)
8 ppm (m, 1H)
6.9 to 7.9 ppm (m, 8H)

Stage (e)

N-o-Chlorobenzyl-2-(thien-2-yl)-ethylamine hydrochloride

A solution of 17.8 g. of the above crude azadiene in 40 ml. ethanol is added dropwise to a solution of 10.2 g. (0.15 mol) sodium borohydride in 160 ml. ethanol.

After the end of the addition, during which the temperature rises from 20° to 30° C., the medium is left to stand at ambient temperature for 2 hours and then heated at 45° to 50° C. for one hour. The reaction mixture is then evaporated and the residue is taken up in water and diisopropyl ether. The aqueous phase is re-extracted with the ether and the combined ether phases are then washed with water, dried over anhydrous sodium sulphate and evaporated. 8.5 ml. of 12 N aqueous hydrochloric acid are added dropwise at 50° C. to the crude base obtained, suspended in 50 ml. of water, and the mixture is then heated to 90° C. The homogeneous solution obtained is treated with animal charcoal and then filtered. Upon cooling, crystals precipitate which are filtered off, washed with softened water and then dried at 50° C. in vacuo to give 15.9 g. (yield: 55%, referred to the diethyl aminomethylphosphonate used in stage a) of N-(o-chlorobenzyl)-2-(thien-2-yl)-ethylamine hydrochloride in the form of white crystals; m.p. 143° C.

| IR (KBr disc) | 3400 cm$^{-1}$, 2900 to 2600 cm$^{-1}$, 1575 cm$^{-1}$ 1450 cm$^{-1}$ |
|---|---|
| NMR (d$_6$-DMSO) | δ/TMS |
| | 7 to 7.8 ppm (m, 8H) |
| | 3.35 ppm (s, 4H) |
| | 4.15 ppm (s, 2H) |
| | about 9 ppm (m, 2H), exchangeable with D$_2$O |

Analysis:
C$_{13}$H$_{14}$ClNS.HCl (M.W. 288.36)

| | | | |
|---|---|---|---|
| calculated: | C 54.16%; | H 5.24%; | N 4.85% |
| found: | 54.11%; | 5.28%; | 4.80% |

EXAMPLE 2

N-(o-Chlorobenzyl-2-[5-tert.-butoxy-(thien-2-yl)]-ethylamine oxalate

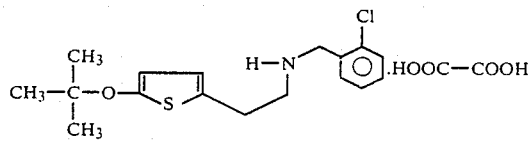

Stage a

Diethyl N-[5-tert.-butoxythien-2-ylidene]-aminomethylphosphonate

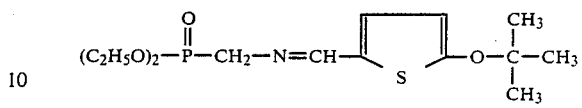

By following the procedure described in Example 1, starting from 18.4 g. (0.1 mol) 5-tert.-butoxythien-2-aldehyde and 16.7 g. (0.1 mol) of diethyl aminomethylphosphonate, there are obtained 33.3 g. (yield: 100%) of the desired imine.

| IR (film) | 3000 cm$^{-1}$ |
|---|---|
| | 1630 cm$^{-1}$ |
| | 1250 cm$^{-1}$, 1,050 cm$^{-1}$ |
| NMR (CDCl$_3$) | δ/TMS |
| | 1.3 ppm (m, 15H) |
| | 4 ppm (m, 6H) |
| | 6.2 ppm (d, 1H) J = 4 Hz ⎫ |
| | 6.7 ppm (d, 1H) J = 4 Hz ⎬ AB system |
| | 8.3 ppm (d, 1H) J = 2 Hz ⎭ |

Stages b, c and d 1-(2-Chlorophenyl)-4-[5-tert.-butoxy-(thien-2-yl)]-2-azabuta-1,3-diene

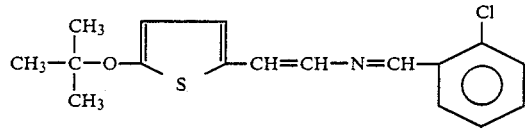

17.85 ml. (0.05 mol) of a 2.8 M solution of n-butyllithium in hexane are added dropwise to a solution of 16.65 g. (0.05 mol) diethyl N-[5-tert.-butoxy-(thien-2-ylidene)]-aminomethylphosphonate in 100 ml. of tetrahydrofuran, the temperature being kept at 25° to 30° C. 30 minutes after the addition has ended, 7 g. (0.05 mol) o-chlorobenzaldehyde in 10 ml. tetrahydrofuran are added dropwise and the reaction mixture is then heated to 45°-50° C. for 1 hour. At the end of this period, the tetrahydrofuran is evaporated off and the residue, when treated as in Example 1, gives 10.6 g. (66.5%) of a yellow-orange oil, which is used as such in the following stage.

Stage e

N-(o-chlorobenzyl)-2-[5-tert.-butoxy-(thien-2-yl)]-ethylamine oxalate

Starting from 10.6 g. (33 millimols) of the 2-azabuta-1,3-diene prepared above and 5.1 g. (75 millimols) sodium borohydride and by following the procedure of Example 1 in 100 ml. of ethanol, there are obtained 10.7 g. of the desired amine in the form of a yellow oil. This oil is dissolved in 50 ml. of acetone and added dropwise to a solution of 3.15 g. (35 millimols) oxalic acid in 50 ml. acetone. After stirring for 2 hours at ambient temperature, the precipitate formed is filtered off, rinsed with acetone and then with diisopropyl ether and finally dried in vacuo at ambient temperature. This gives 10.4 g. (yield: 50%, referred to the diethyl aminomethylphosphonate) of N-(o-chlorobenzyl)-2-[5-tert.-butoxy-(thien-2-yl)]-ethylamine oxalate in the form of white crystals; m.p. 202° C. (decomposition).

| IR (film, on the base) | 3300 cm$^{-1}$, 2850 cm$^{-1}$, 3000 cm$^{-1}$ |
| --- | --- |
| | 1560 cm$^{-1}$, 1150 cm$^{-1}$ |
| NMR (CDCl$_3$) | δ/TMS |
| 1.3 ppm (s, 9H) | (CH$_3$)$_3$C |
| 1.7 ppm (s, 1H) | exchangeable with D$_2$O |
| 2.8 ppm (s, 4H) | 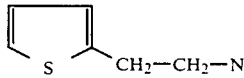 |
| 3.85 ppm (s, 2H) | —N—CH$_2$—Ar |
| 6.05 ppm (d, 1H) | |
| 6.35 ppm (d, 1H) | |
| 7.2 ppm (m, 4H) | AB system with J$_{AB}$ = 4 Hz |

Analysis:

C$_{17}$H$_{22}$ClNOS.C$_2$H$_2$O$_4$ (M.W. 413.917)
 calculated: C 55.13%; H 5.81%; N 3.38%
 found: 55.25%; 5.75%; 3.36%

EXAMPLE 3

N-Furfuran-2-yl-1-(thien-2-yl)-ethylamine oxalate

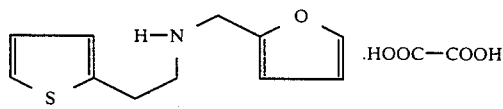

Diethyl N-thien-2-ylidene-aminomethylphosphonate 0.1 mol of the desired product is prepared by following the procedure described in Example 1.

Stages b, c and d 1-(Furan-2-yl)-4-(thien-2-yl)-2-azabuta-1,3-diene

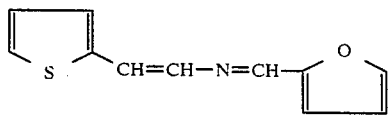

A solution of 26.1 g. (0.1 mol) diethyl N-(thien-2-ylidene)-aminomethylphosphonate in 40 ml. tetrahydrofuran is added dropwise to a suspension of 4.8 g. (0.1 mol) sodium hydride (50% dispersion in oil) in 100 ml. tetrahydrofuran. After the end of the addition, during which the temperature has risen from 20° to 30° C., the medium is heated at 45° C. for 2 hours and a solution of 9.6 g. (0.1 mole) furfural in 20 ml. tetrahydrofuran is then added dropwise thereto. The medium is subsequently kept at 45–50° C. for 2 hours, with stirring, and the reaction mixture is then treated as described in Example 1. This gives 17.85 g. (yield: 88%) of the desired 2-azabuta-1,3-diene in the form of an orange oil, which is used as such in the following stage.

Stage e

N-Furfuran-2-yl-2-(thien-2-yl)-ethylamine oxalate

The azadiene obtained above is dissolved in 200 ml. ethanol and treated with 6.7 g. (0.176 mol) sodium borohydride as described in Example 2. The crude base obtained is dissolved in 50 ml. of acetone and added to a solution of 8 g. oxalic acid in 50 ml. acetone. After stirring for 2 hours at ambient temperature, the precipitate is filtered off, rinsed with acetone and then recrystallised from a water/ethanol mixture (60/40 v/v) to give 17.52 g. (yield: 59%, referred to the diethyl aminomethylphosphonate) of N-furfuran-2-yl-2-(thien-2-yl)-ethylamine oxalate in the form of crystals; m.p. 215° C.

| IR (KBr disc) | 3400 cm$^{-1}$, 3040 cm$^{-1}$, 2850 cm$^{-1}$ |
| --- | --- |
| | 1715 cm$^{-1}$, 1650 cm$^{-1}$, 1480 cm$^{-1}$ |
| NMR (CDCl$_3$, on the base freed from the oxalate) δ/TMS | |
| 1.65 ppm (s, 1H), | exchangeable with D$_2$O |
| 2.8 ppm (s, 4H) | 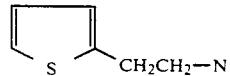 |
| 3.65 ppm (s, 2H) | 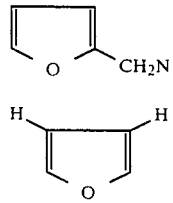 |
| 6.1 ppm (m, 2H) | 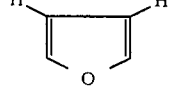 |
| 6.6 to 7.3 ppm (m, 4H) | |

Analysis:

C$_{11}$H$_{13}$NOS.C$_2$H$_2$O$_4$ (M.W. 297.324)
 calculated: C 52.52%; H 5.05%; N 4.71%
 found: 52.45%; 5.01%; 4.63%

EXAMPLE 4

N-(o-Nitrobenzyl)-2-(thien-2-yl)-ethylamine hydrochloride

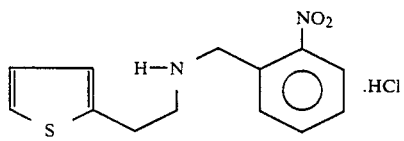

Stage a

Diethyl N-thien-2-ylidene-aminomethylphosphonate 0.1 mol of the desired product is prepared by following the procedure described in Example 1.

Stages b, c and d 1-(o-Nitrophenyl)-4-(thien-2-yl)-2-azabuta-1,3-diene

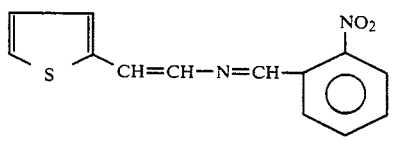

By following the procedure described in Example 1, there are obtained 22 g. (yield: 85%) of the desired azadiene in the form of an orange oil, which is used as such in the following stage.

Stage e

N-(o-Nitrobenzyl)-2-(thien-2-yl)-ethylamine hydrochloride 11.56 g. (0.17 mol) sodium borohydride are added in small portions to the azadiene obtained above, dissolved in 200 ml. of ethanol, the temperature being kept below 25° C. The reaction medium is subsequently stirred for 2 hours at ambient temperature and then poured into 1 liter of water and extracted with chloroform.

The organic phase is washed with water, dried over anhydrous sodium sulphate and then evaporated to give the desired base in the form of an oil which is coverted to the hydrochloride in ethanol. The precipitate formed is recrystallised from ethanol. This gives 18.2 g. (yield: 61%, referred to the diethyl aminomethylphosphonate) of N-(o-nitrobenzyl)-2-(thien-2-yl)-ethylamine hydrochloride in the form of white crystals; m.p. 168° C.

| | |
|---|---|
| IR (KBr disc) | 3450 cm$^{-1}$, 3000-2900 cm$^{-1}$, 2700 cm$^{-1}$ 1560-1525 cm$^{-1}$, 1450 cm$^{-1}$, 1340 cm$^{-1}$ |
| NMR (CDCl$_3$, on the base freed from the hydrochloride) δ/TMS | |
| 1.65 ppm (s, 1H), | exchangeable with D$_2$O |
| 2.9 ppm (t, 4H) | 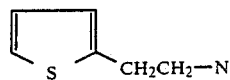 |
| 4 ppm (s, 2H) | N—CH$_2$—Ar |
| 6.7 to 7.9 ppm (m, 7H), aromatic protons | |

Analysis:
C$_{13}$H$_{14}$N$_2$OS.HCl (M.W. 298.773)
calculated: C 52.26%; H 5.06%; N 9.38%
found: 52.28%; 5.03%, 9.31%

EXAMPLE 5

N-(Picolin-4-yl)-2-(thien-2-yl)-ethylamine

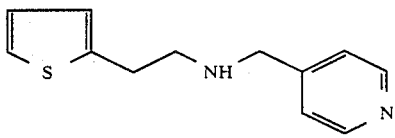

Stage a

Diethyl N-(thien-2-ylidene)-aminomethylphosphonate 0.1 mol of the desired product is prepared by following the procedure described in Example 1.

Stages b, c and d 1-(Pyridin-4-yl)-4-(thien-2-yl)-2-azabuta-1,3-diene

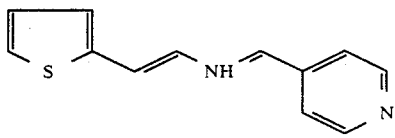

By following the procedure of Example 1, starting from 0.1 mol diethyl N-(thien-2-ylidene)-aminomethylphosphonate and 0.1 mol pyridin-4-yl-carboxaldehyde, there are obtained 18 g. (yield: 85%) of the desired azadiene in the form of an orange oil, which is used as such in the following step.

A pure sample of the azadiene is obtained by chromatography on silica (eluent: ethyl acetate/hexane, 50/50).

The orange crystals obtained have the following characteristics:

| | | |
|---|---|---|
| Melting point = 165° C. | | |
| NMR (CDCl$_3$) δ/TMS | 6.5 to 7.5 ppm (m, 7H) | |
| | 8.4 ppm (s, 1H) | CH=N |
| | 8.45 ppm (d, 2H) | A part of the AB system of the pyridine |
| IR (KBr disc) | 1600 cm$^{-1}$ | |
| | 1560 cm$^{-1}$ | |
| | 1420 cm$^{-1}$ | |

Stage e

N-(Picolin-4-yl)-2-(thien-2-yl)-ethylamine

The crude azadiene obtained above is reduced with sodium borohydride under the conditions described in Example 4 to give, after purification by chromatography on silica, 9.16 g. (yield: 42%, referred to the diethyl aminomethylphosphonate) of the desired product in the form of a light yellow oil, which turns brown in the air.

| | |
|---|---|
| IR (film) | 3300 cm$^{-1}$ |
| | 2900 cm$^{-1}$ |
| | 1600 cm$^{-1}$ |
| | 1440 cm$^{-1}$ |
| NMR (CDCl$_3$) δ/TMS | 1.7 ppm (s, 1H), exchangeable with D$_2$O |
| | 3 ppm (t, 4H) Ar—CH$_2$—CH$_2$—N |
| | 3.8 ppm (s, 2H) Ar—CH$_2$—N |
| | 6.6 to 7.4 ppm (m, 5H) |
| | 8.4 ppm (d, 2H) |

EXAMPLE 6

N-Thien-2-yl-2-(thien-2-yl)-ethylamine hydrochloride

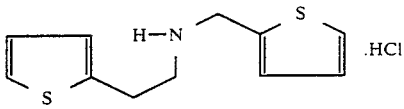

Stage a

Diisopropyl N-thien-2-ylidene-aminomethylphosphonate.

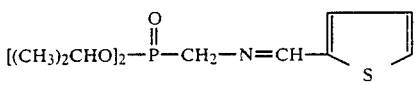

0.1 mol of the desired product is prepared by following the procedure described in Example 1.

| | |
|---|---|
| IR (film): | 1635, 1260, 1080-1060 cm$^{-1}$ |
| NMR (CDCl$_3$): | δ/TMS |
| 1.3 ppm (d, 12H) | 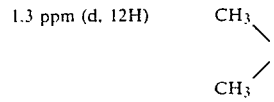 |

| 4.05 ppm (d, 2H) | P—CH₂N= |
| --- | --- |
| 4.75 ppm (m, 2H) | C\\CH—O/C |
| 7 to 7.6 ppm (m, 3H) | |
| 8.35 ppm (d, 1H) | Ar—CH=N |

Stages b, c and d 1-(Thien-2-yl)-4-(thien-2-yl)-2-azabuta-1,3-diene

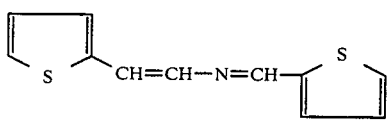

By following the procedure described in Example 1, 13.6 g. (yield: 62%) of the desired azadiene are obtained in the form of yellow crystals, after recrystallisation from methanol; m.p. 163° C.

| IR (KBr disc): | C=N 1635 cm⁻¹ |
| --- | --- |
| NMR (d₆-DMSO) | δ/TMS |
| | 8.35 ppm (s, 1H) |
| | 6.9 to 7.5 ppm (m, 8H) |
| Analysis: | |
| C₁₁H₉NS₂ (M.W. 219.32) | | |
| calculated: | C 60.27%; | H 4.10%; | N 6.39% |
| found: | 60.25%; | 4.07%; | 6.40% |

Stage e

N-Thien-2yl-2-(thien-2-yl)-ethylamine hydrochloride

By following the procedure described in Example 1, using 10.95 g. (0.05 mol) of the azadiene prepared above, there are obtained 11.15 g. (yield: 53%, referred to the diisopropyl aminomethylphosphonate) of N-thien-1-yl-2-(thien-2-yl)-ethylamine hydrochloride in the form of white crystals, after conversion into the hydrochloride in diisopropyl ether; m.p. 230° C. (decomposition).

| IR (KBr disc) | 3400 cm⁻¹ |
| --- | --- |
| | 2920 cm⁻¹ |
| | 2750 cm⁻¹ |
| | 1440 cm⁻¹ |
| | 1250 cm⁻¹ |
| NMR (d₆-DMSO) | δ/TMS |
| | 6.9 to 7.5 ppm (m, 6H) |
| | 4.40 ppm (s, 2H) |
| | 3.2 ppm (m, 4H) |
| | about 9 ppm (m, 2H), exchangeable with D₂O |
| Analysis: | |
| C₁₁H₁₃NS₂.HCl (M.W. 259.815) | | |
| calculated: | C 50.86%; | H 5.39%; | N 5.39% |
| found: | 50.90%; | 5.40%; | 5.37% |

EXAMPLE 7

Preparation of N-(o-chlorobenzyl)-2-(thien-3-yl)-ethylamine hydrochloride

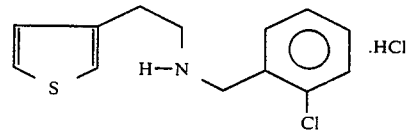

Stage a

Diethyl N-thien-3-ylidene-aminomethylphosphonate 0.1 mol of the desired product is prepared by following the procedure desribed in Example 1.

| IR (film): | 1635 cm⁻¹, 1250 cm⁻¹, 1050 cm⁻¹ |
| --- | --- |
| NMR (CDCl₃) | δ/TMS |
| | 1.3 ppm (t, 6H) |
| | 4 ppm (m, 6H) |
| | 7.2 to 7.6 ppm (m, 3H) |
| | 8.3 ppm (d, 1H) |

Stages b, c and d 1-(o-Chlorophenyl)-4-(thien-3-yl)-2-azabuta-1,3-diene

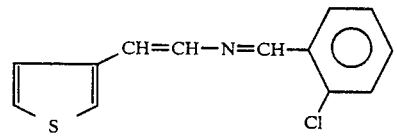

By following the procedure of Example 1 but using o-chlorobenzaldehyde, 17.3 g. (yield:71%) of the desired 2-azabuta-1,3-diene are obtained in the form of a yellow oil, after treatment, and this is reacted as such in the following stage.

Stage e

N-(o-Chlorobenzyl)-2-(thien-3-yl)-ethylamine hydrochloride

By following the procedure of Example 1 on the product prepared above, 15.1 g. (yield: 52%, referred to the aminomethylphosphonate used in stage a) of the desired hydrochloride are obtained in the form of white crystals; m.p. 176° C.

| IR (KBr disc): | 3400, 2900, 2800–2700, 1575, 1450 cm⁻¹ |
| --- | --- |
| NMR (d₆-DMSO) | δ/TMS |
| | 3.2 ppm (s, 4H) |
| | 4.05 ppm (s, 2H) |
| | 6.9 to 7.8 ppm (m, 7H) |
| | about 9 ppm (m, 2H) exchangeable with D₂O |
| Analysis: | |
| C₁₃H₁₄ClNS.HCl (M.W. 288.236) | | |
| calculated: | C 54.16%; | H 5.24%; | N 4.85% |
| found: | 54.25%; | 5.20%; | 4.79% |

EXAMPLE 8

Preparation of N-(o-chlorobenzyl)-2-(thien-2-yl)-ethylamine hydrochloride

Stage a

Isopropyl N-thien-2-ylidene-aminomethyl-phenylphosphinate

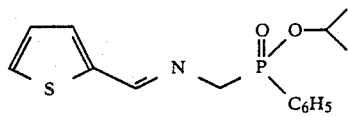

0.1 mol of the desired product is prepared by following the procedure described in Example 1.

| IR (film) | C=N | 1625 cm$^{-1}$ |
| --- | --- | --- |
| | | 1430 cm$^{-1}$ |
| | | 1200 cm$^{-1}$ |
| | | 980 cm$^{-1}$ |
| NMR (CDCl$_3$) | δ/TMS | |
| | | 1.4 ppm (dd, 6H) |
| | | 4.15 ppm (d, 2H) |
| | | 4.75 ppm (m, 1H) |
| | | 7 to 8 ppm (m, 8H) |
| | | 8.25 ppm (d, 1H) |

Stages b and c

Isopropyl N-[8-(thien-2-yl)-vinyl]-amino-phenylphosphinate

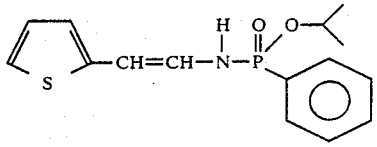

Starting from 0.1 mol of the imine prepared above and following the procedure of Example 1, 18.6 g. (yield: 60.5%) of the desired product are obtained in the form of crystals; m.p. 125° C.

| IR (KBr disc): | 3400-3150 cm$^{-1}$ |
| --- | --- |
| | 1650 cm$^{-1}$ |
| | 1220 cm$^{-1}$ |
| | 1999 cm$^{-1}$ |
| NMR (CDCl$_3$) | δ/TMS |
| | 1.35 ppm (d, 6H) |
| | 4.8 ppm (m, 1H) |
| | 5.9 ppm (m, 1H) |
| | 6.2 to 7 ppm (m, 4H) |
| | 7 to 8 ppm (m, 6H), 1H exchangeable with D$_2$O |

Stage d 1-(o-Chlorophenyl)-4-(thien-2-yl)-2-azabuta-1,3-diene

A solution of 0.06 mol of the phosphinate prepared in the previous stage, in 20 ml. tetrahydrofuran, is added dropwise to a suspension of 0.06 mol sodium hydride (50% dispersion in oil) in 50 ml. tetrahydrofuran. When the addition has ended, the temperature of the reaction medium is increased to 40° C. to 45° C. for 30 minutes and a solution of 0.06 mol o-chlorobenzaldehyde in 20 ml. tetrahydrofuran is then added dropwise. Stirring is continued for 1 hour at 40°-45° C. and then, after cooling, the reaction mixture is poured into water and extracted with diisopropyl ether. The organic phases are washed with a saturated aqueous solution of sodium chloride, dried over anhydrous sodium sulphate and evaporated to give 14.1 g. (yield: 95%, referred to the phosphinate used) of the desired azadiene.

A sample purified on a silica column (eluent: hexane, 95%/ethyl acetate, 5%) shows that the product obtained is identical to that prepared in Example 1: IR and NMR are identical. Same Rf values in LC, GC and TLC.

Stage e

N-(o-Chlorobenzyl)-2-(thien-2yl)-ethylamine hydrochloride

Reduction of the azadiene obtained in the previous stage, under the conditions described in Example 1, gives, after similar treatments, 14.7 g. (yield: 51%, referred to the aminomethylphosphinate) of N-(o-chlorobenzyl)- 2-(thien-2-yl)-ethylamine hydrochloride, the physical, spectral and analytical characteristics of which are identical to those of the product obtained in Example 1.

We claim:

1. Process for the preparation of 3-(thien-2-yl)- and 2-(thien-3-yl)-ethylamine derivatives of the formula:

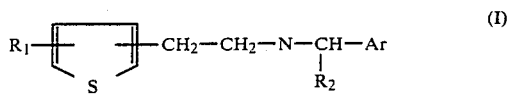

in which R$_1$, in the 2-, 3-, 4-or 5-position, is a member selected from the group consisting of hydrogen, halogen, nitro, amino, cyano, carboxyl, a linear or branched lower alkyl, lower alkoxy, a monocyclic heterocyclic or non-heterocyclic aromatic radical, which is optionally mono-or disubstituted with a member selected from the group consisting of lower alkyl, phenyl, halogen, nitro, cyano, amino, carboxy and lower alkoxy, R$_2$ is a member selected from the group consisting of hydrogen atom, a linear or branched lower alkyl, monocyclic heterocyclic or non-heterocyclic aromatic radical, which is optionally mono- or disubstituted with a member selected from the group consisting of lower alkyl, phenyl, halogen, nitro, cyano, amino, carboxyl and lower alkoxy, and Ar is a monocyclic heterocyclic or non-heterocyclic aromatic radical, which is optionally mono- or disubstituted with a member selected from the group consisting of lower alkyl, phenyl, halogen, nitro, cyano, amino, carboxyl and lower alkoxy, which comprise the steps of reacting a compound of the formula:

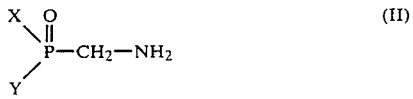

in which X and Y, which can be the same or different, are members selected from the group consisting of lower alkyl, lower alkoxy, aryl, aryloxy, diarylamino or dialkylamino, with a carbonyl compound of the formula:

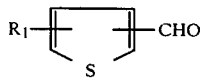 (III)

in which $R_1$ is as defined above, to give a compound of the formula:

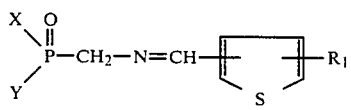 (IV)

in which X, Y and $R_1$ are as defined above, treating the resulting compound with a base $B^-M^+$ to give a carbanion of the formula:

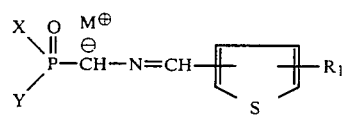 (V)

in which X, Y and $R_1$ are as defined above, heating the resulting compound so as to form a compound of the formula:

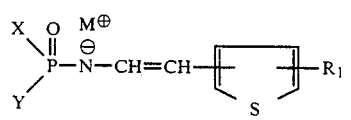 (VI)

in which X, Y and $R_1$ are as defined above, treating the resultant compound with water so as to form a compound of the formula:

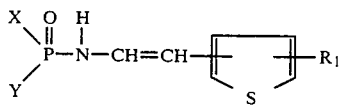 (VII)

in which X, Y and $R_1$ are as defined above, successively treating the resulting compound with a base $B'^-M'^+$ and then with a carbonyl compound of the general formula:

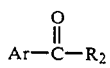 (VIII)

in which Ar and $R_2$ are as defined above, to give a compound of the formula:

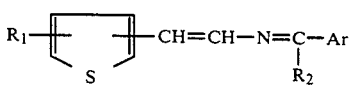 (IX)

in which $R_1$, $R_2$ and Ar are as defined above, and then, treating the resulting compound with a reducing agent so as to form a compound of the formula (I).

2. Process according to claim 1, wherein the reaction of the organophosphorus compound (II) with the carbonyl derivative (III) is catalysed by a mineral or organic acid.

3. Process according to claim 2, wherein the acid used is p-toluenesulphonic acid.

4. Process according to claim 1 or 2, wherein the conversion of the carbanion (V) into the compound (VII) is carried out in a single operation without isolation of an intermediate.

5. Process according to claim 4, wherein the reaction is carried out at a temperature of from −78° C. to +150° C.

6. Process according to claim 5, wherein the temperature used is at the top of the given range.

7. Process according to claim 1, wherein the reduction of the derivative (IX) is carried out with a mixed alkali metal hydride.

8. Process according to claim 7, wherein the hydride used is sodium or potassium borohydride.

9. Process for the preparation of 3-(thien-2-yl)- and 2-(thien-3-yl)-ethylamine derivatives of the formula:

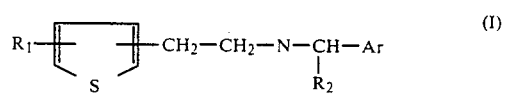 (I)

in which $R_1$, in the 2-, 3-, 4- or 5-position, is hydrogen, halogen, nitro, a linear or branched lower alkyl, lower alkoxy, thienyl, furyl, pyridyl, phenyl or naphthyl group, which is optionally mono- or disubstituted with a member selected from the group consisting of lower alkyl, phenyl, halogen, nitro and lower alkoxy, $R_2$ is a member selected from the group consisting of hydrogen atom, a linear or branched lower alkyl, thienyl, furyl, pyridyl, phenyl or naphthyl, which is optionally mono- or disubstituted with a member selected from the group consisting of lower alkyl, phenyl, halogen, nitro, and lower alkoxy, and Ar is a thienyl, furyl, pyridyl, phenyl or naphthyl, which is optionally mono- or disubstituted with a member selected from the group consisting of lower alkyl, phenyl, halogen, nitro, and lower alkoxy, which comprise the steps of reacting a compound of the formula:

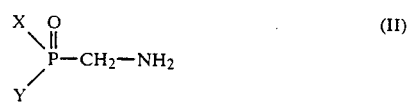 (II)

in which X and Y, which can be the same or different, are members selected from the group consisting of lower alkyl, lower alkoxy, aryl, aryloxy, diarylamino or dialkylamino, with a carbonyl compound of the formula:

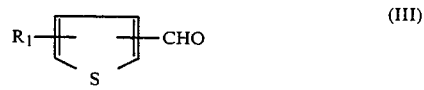 (III)

in which $R_1$ is as defined above, to give a compound of the formula:

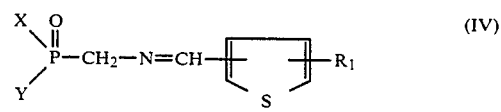 (IV)

in which X, Y and R₁ are as defined above, treating the resulting compound with a base B⁻M⁺ to give a carbanion of the formula:

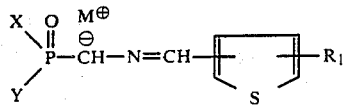  (V)

in which X, Y and R₁ are as defined above, heating the resulting compound so as to form a compound of the formula:

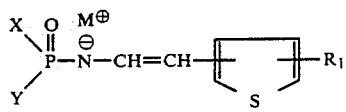  (VI)

in which X, Y and R₁ are as defined above, treating the resultant compound with water so as to form a compound of the formula:

$$\begin{array}{c} X \\ \diagdown \\ Y \end{array} \overset{O}{\underset{\|}{P}} \overset{H}{\underset{|}{-N}}-CH=CH-\!\!\!\begin{array}{c}\phantom{x}\\S\end{array}\!\!\!-R_1 \quad (VII)$$

in which X, Y and R₁ are as defined above, successively treating the resulting compound with a base B′⁻M′⁺ and then with a carbonyl compound of the general formula:

  (VIII)

in which Ar and R₂ are as defined above, to give a compound of the formula:

$$R_1-\!\!\!\begin{array}{c}\phantom{x}\\S\end{array}\!\!\!-CH=CH-N=\underset{\underset{R_2}{|}}{C}-Ar \quad (IX)$$

in which R₁, R₂ and Ar are as defined above, and then, treating the resulting compound with a reducing agent so as to form a compound of the formula (I).

10. N-(o-Chlorobenzyl)-2- ethylamine.

* * * * *